(12) United States Patent
Hou et al.

(10) Patent No.: US 10,624,525 B2
(45) Date of Patent: Apr. 21, 2020

(54) ENDOSCOPIC SYSTEM AND METHOD FOR CONTROLLING THE SAME

(71) Applicant: HIWIN TECHNOLOGIES CORP., Taichung (TW)

(72) Inventors: Jung-Fu Hou, Taichung (TW); Hung-Chuan Hsu, Taichung (TW); You-Min Chen, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 428 days.

(21) Appl. No.: 15/584,574

(22) Filed: May 2, 2017

(65) Prior Publication Data

US 2018/0317753 A1   Nov. 8, 2018

(51) Int. Cl.

| | |
|---|---|
| *A61B 1/00* | (2006.01) |
| *A61B 1/04* | (2006.01) |
| *G06T 7/73* | (2017.01) |
| *A61B 34/30* | (2016.01) |
| *A61B 90/50* | (2016.01) |
| *A61B 34/20* | (2016.01) |

(52) U.S. Cl.
CPC ........ *A61B 1/00009* (2013.01); *A61B 1/0002* (2013.01); *A61B 1/00006* (2013.01); *A61B 1/0016* (2013.01); *A61B 1/00149* (2013.01); *A61B 1/04* (2013.01); *A61B 34/30* (2016.02); *A61B 90/50* (2016.02); *G06T 7/73* (2017.01); *A61B 2034/2065* (2016.02); *G06T 2207/10068* (2013.01); *G06T 2207/30004* (2013.01)

(58) Field of Classification Search
CPC combination set(s) only.
See application file for complete search history.

(56) References Cited

U.S. PATENT DOCUMENTS

| | | | | |
|---|---|---|---|---|
| 9,259,289 | B2 * | 2/2016 | Zhao | B25J 9/1689 |
| 2010/0274087 | A1 * | 10/2010 | Diolaiti | A61B 90/37 |
| | | | | 600/118 |
| 2010/0331855 | A1 * | 12/2010 | Zhao | A61B 34/30 |
| | | | | 606/130 |

(Continued)

FOREIGN PATENT DOCUMENTS

| | | | |
|---|---|---|---|
| DE | 202014010578 U1 | | 1/2016 |
| JP | 2015213753 A | | 12/2015 |

(Continued)

OTHER PUBLICATIONS

Search Report appended to an Office Action issued to Taiwanese counterpart application No. 105141018 by the TIPO dated Mar. 16, 2017 (2 pages, English translation included).

*Primary Examiner* — John P Leubecker
*Assistant Examiner* — Shankar Raj Ghimire
(74) *Attorney, Agent, or Firm* — Michael Best & Friedrich LLP (57) ABSTRACT

An endoscopic system includes a mechanical arm, an endoscope and a control unit. The endoscope is held by the mechanical arm, and is configured to capture an image. The control unit is electrically connected to the mechanical arm and the endoscope, and is configured to receive and process the image captured by the endoscope, to determine whether the image has at least two specific instruments that are arranged in a specific configuration, and to drive the mechanical arm to move the endoscope when the determination is affirmative.

8 Claims, 9 Drawing Sheets

(56) References Cited

U.S. PATENT DOCUMENTS

| | | | |
|---|---|---|---|
| 2012/0209288 A1* | 8/2012 | Robinson | A61B 34/30 |
| | | | 606/130 |
| 2013/0002844 A1* | 1/2013 | Shida | A61B 1/00009 |
| | | | 348/65 |
| 2015/0085092 A1* | 3/2015 | Takemura | A61B 1/00009 |
| | | | 348/65 |
| 2016/0174955 A1* | 6/2016 | Frimer | A61B 1/00149 |
| | | | 600/424 |
| 2016/0235486 A1* | 8/2016 | Larkin | B25J 9/1671 |
| 2016/0342847 A1* | 11/2016 | Song | G06K 9/66 |
| 2016/0354166 A1* | 12/2016 | Popovic | A61B 34/30 |
| 2017/0172662 A1* | 6/2017 | Panescu | A61B 90/37 |
| 2017/0189126 A1* | 7/2017 | Weir | B25J 9/1669 |
| 2018/0324414 A1* | 11/2018 | Hoffman | A61B 1/00039 |

FOREIGN PATENT DOCUMENTS

| | | |
|---|---|---|
| JP | 2017505202 A | 2/2017 |
| TW | 201641071 A | 12/2016 |
| WO | 2015121765 A1 | 8/2015 |

* cited by examiner

ENDOSCOPIC SYSTEM AND METHOD FOR CONTROLLING THE SAME

FIELD

The disclosure relates to an endoscopic system and a method for controlling the same.

BACKGROUND

U.S. Patent Application Publication No. 201408632 A1 discloses a surgical controlling system that includes an endoscope providing a real-time image of surgical environment of a human body, and a processing means. The processing means is adapted to process the real-time image to determine positions of elements (i.e., two surgical instruments) within the real-time image. According the positions of the two surgical instruments, the surgical controlling system can automatically move the endoscope to a position such that a central point of the real-time image is at a middle point between the two surgical instruments. The distance between the two surgical instruments may vary frequently during a surgical operation, so the endoscope may be moved frequently. However, some of the moves of the endoscope are undesirable and may disrupt the surgical operation.

SUMMARY

Therefore, an object of the disclosure is to provide an endoscopic system that can alleviate the drawback of the prior art.

According to the disclosure, the endoscopic system includes a mechanical arm, an endoscope and a control unit The mechanical arm includes a base, a kinematic chain and a holding part. The kinematic chain is connected to the base and is movable with respect to the base. The holding part is connected to an end of the kinematic chain opposite to the base The endoscope is held by the holding part, and is configured to capture an image The control unit is electrically connected to the kinematic chain and the endoscope. The control unit is configured to receive and process the image captured by the endoscope, to determine whether the image has at least two specific instruments that are arranged in a specific configuration, and to drive the kinematic chain to move the endoscope when the determination is affirmative Another object of the disclosure is to provide a method for controlling an endoscopic system that can alleviate the drawback of the prior art According to the disclosure, the method for controlling an endoscopic system is provided. The endoscopic system includes a mechanical arm, an endoscope held by the mechanical arm, and a control unit electrically connected to the mechanical arm and the endoscope. The method includes the steps of:

capturing, by the endoscope, an image;

processing, by the control unit, the image captured by the endoscope to determine whether the image has at least two specific instruments that are arranged in a specific configuration; and driving, by the control unit, the mechanical arm to move the endoscope when the determination made in the previous step is affirmative.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1:
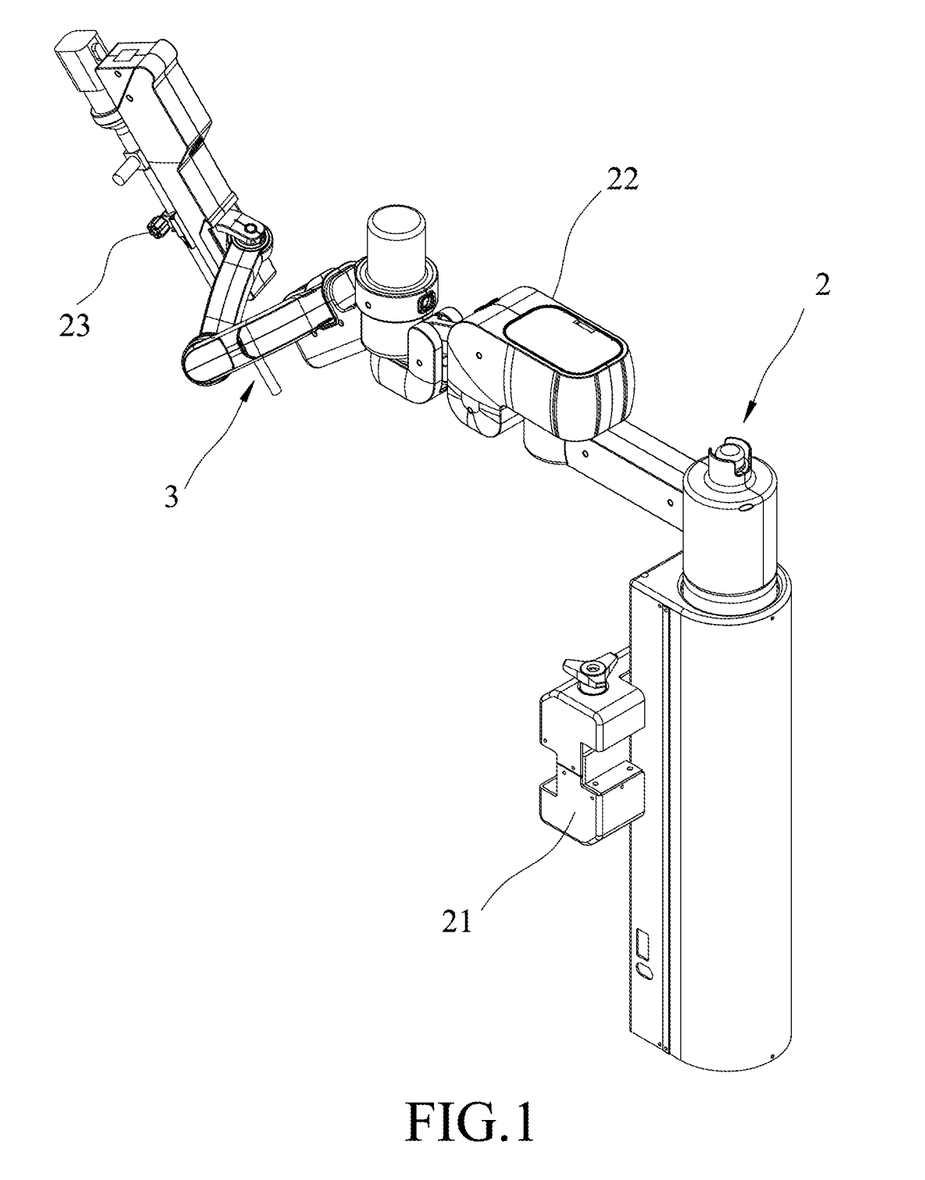
FIG. 1 is a perspective view of a part of one embodiment of an endoscopic system according to the disclosure.
Figure 2:
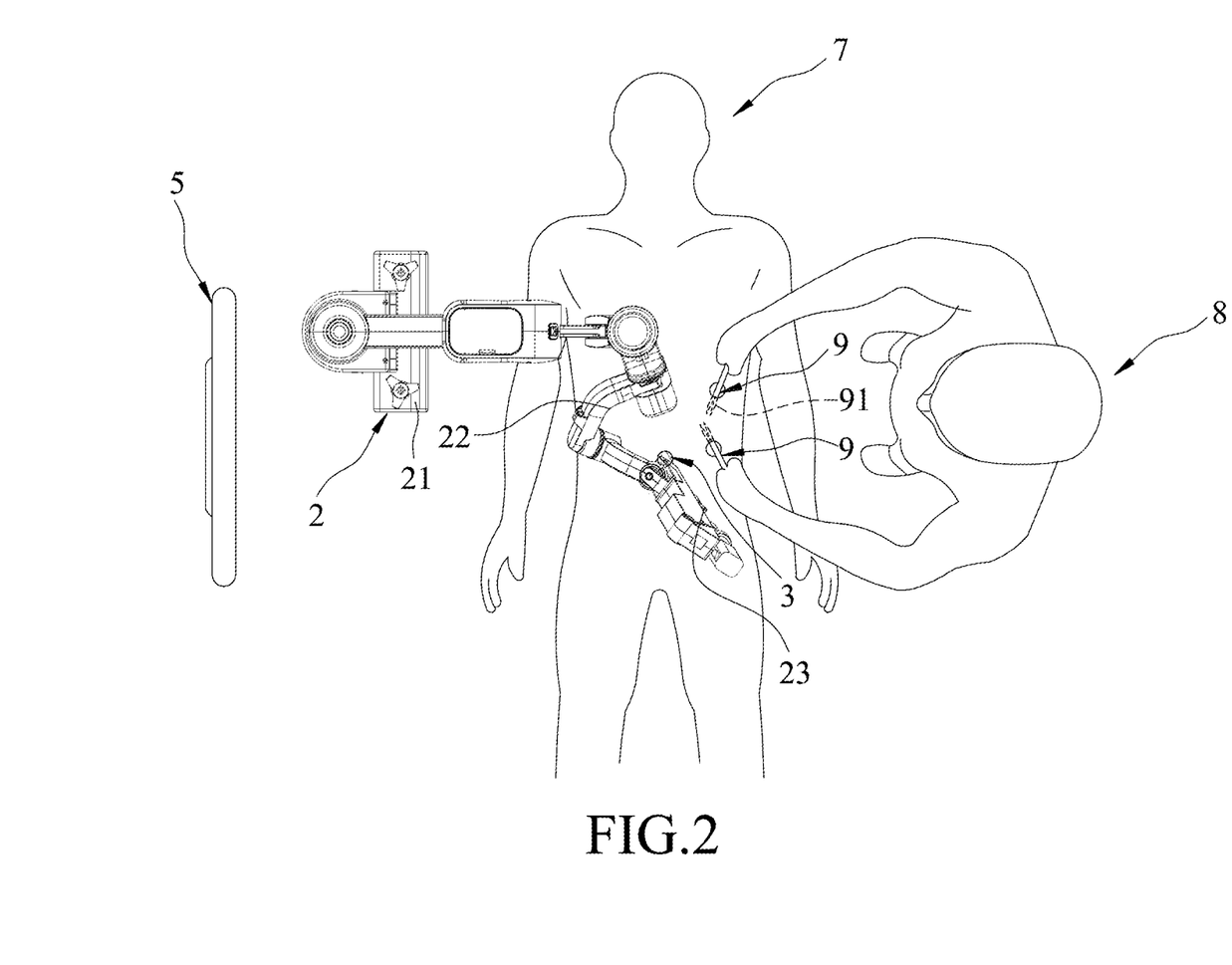
FIG. 2 is a top view of the endoscopic system used in an endoscopic surgery.
Figure 3:
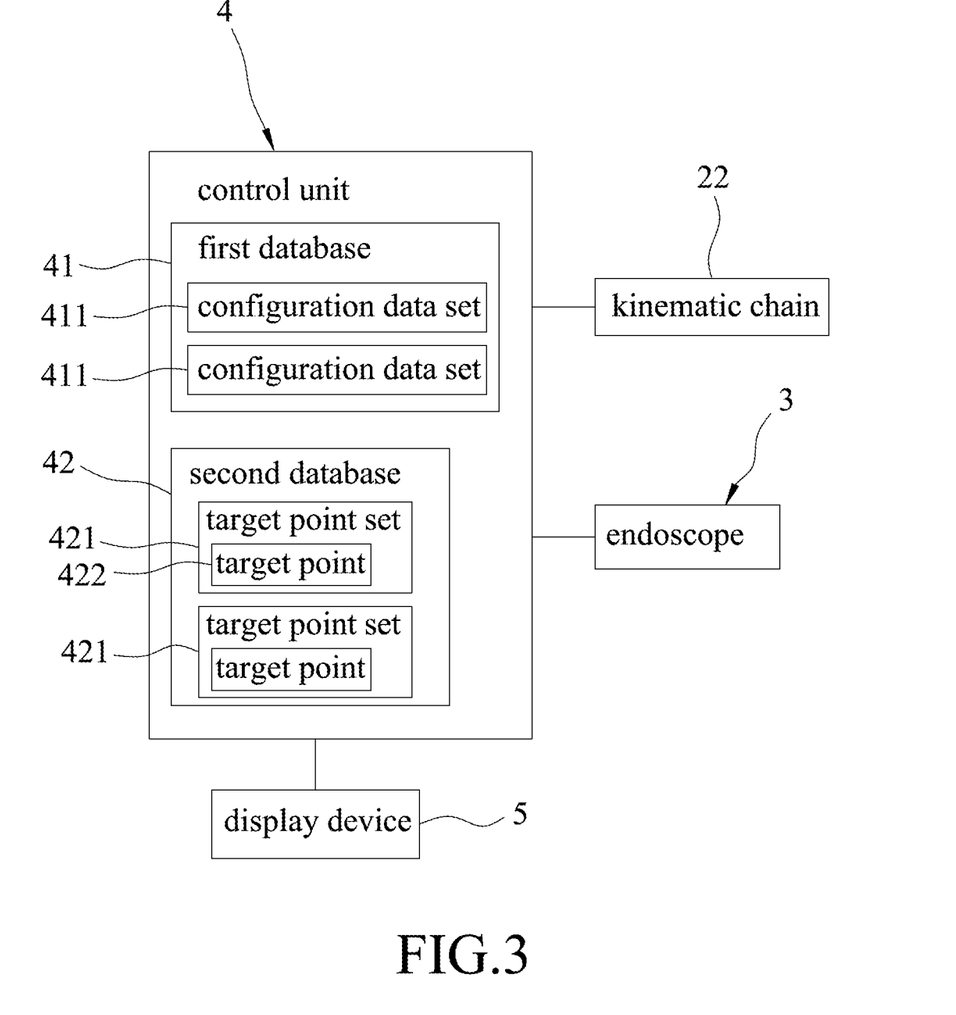
FIG. 3 is a block diagram of a part of the endoscopic system.

Referring to FIGS. 1 to 3, the embodiment of an endoscope system according to this disclosure includes a mechanical arm 2, an endoscope 3, a control unit 4 and a display device 5. The endoscope system is configured to cooperate with two specific instruments 9. Each of the specific instruments 9 includes a working end 91. For example, the specific instruments 9 are, but not limited to, surgical instruments in this embodiment.

The mechanical arm 2 includes a base 21, a kinematic chain 22 and a holding part 23. The kinematic chain 22 is connected to the base 21, and is movable with respect to the base 21. The holding part 23 is connected to an end of the kinematic chain 22 opposite to the base 21.

The endoscope 3 is held by the holding part 23, and is configured to capture an image.

Figure 5:
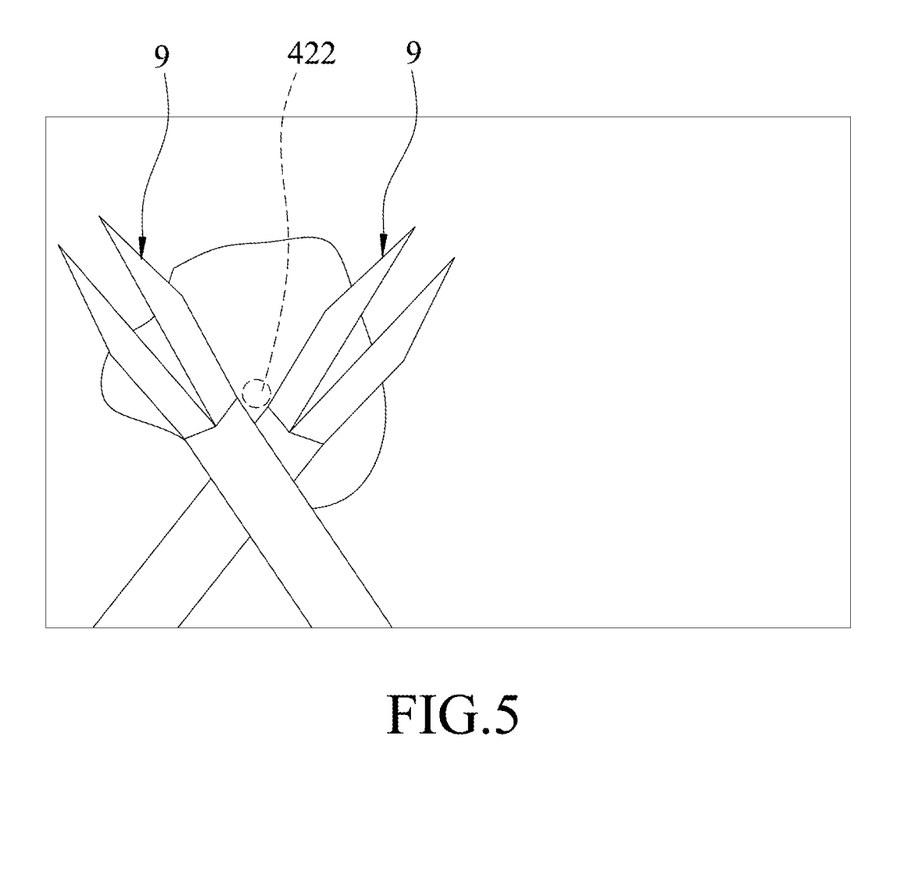
Figure 6:
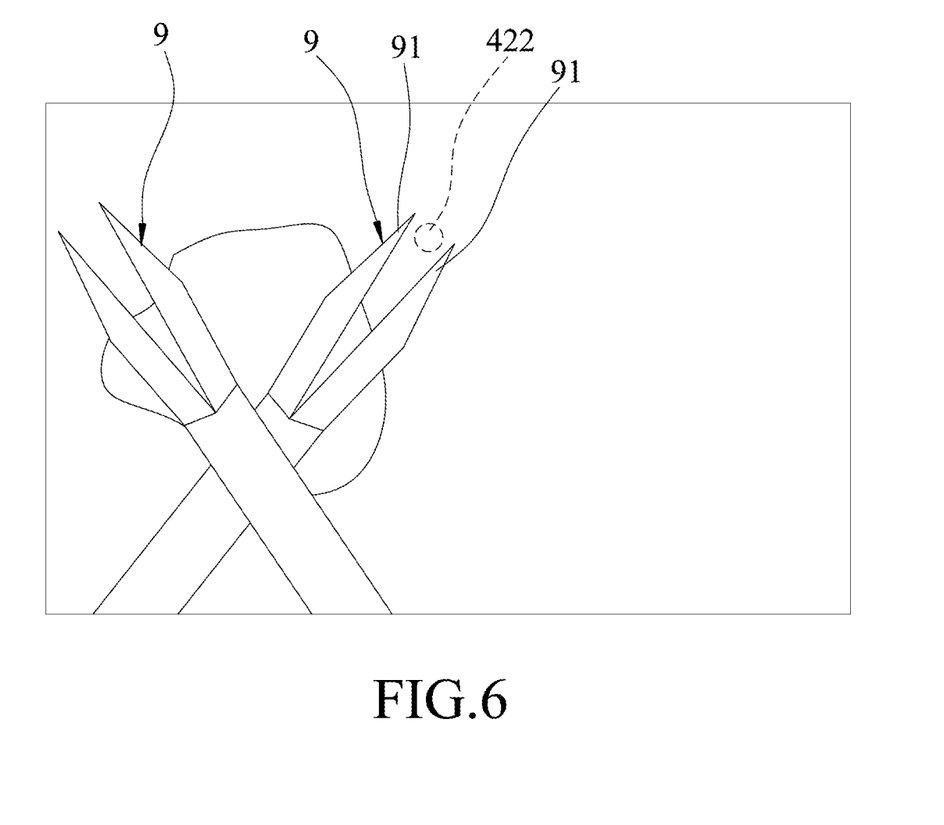

The control unit 4 is electrically connected to the kinematic chain 22, the endoscope 3 and the display device 5. The control unit 4 includes a first database 41 and a second database 42. The first database 41 stores a plurality of configuration data sets 411 that are representative of reference configurations associated respectively with different relative arrangements of the specific instruments 9, respectively. The second database 42 stores a plurality of target point sets 421. Each of the target point sets 421 corresponds to a respective one of the configuration data sets 411, and includes at least one target point 422 that is located at a predetermined position with respect to the relative arrangement of the specific instruments 9 with which the reference configuration that is represented by the respective one of the configuration data sets 411 is associated. FIGS. 5 and 6 depict exemplary visualization of two different target points 422 with respect to respective relative arrangements of the specific instruments 9.

Figure 4:
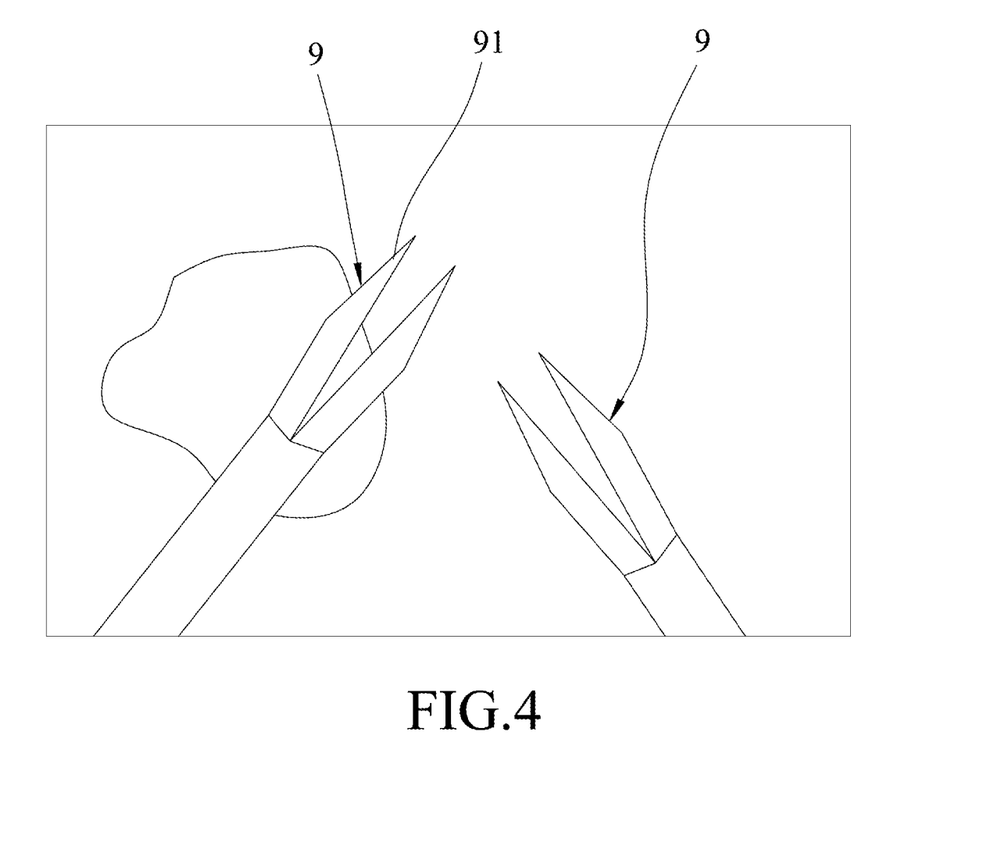
FIGS. 4 to 7 are schematic diagram illustrating images by an endoscope of the endoscopic system during the endoscopic surgery.

Referring to FIGS. 2 to 4, the control unit 4 is configured to receive and process the image captured by the endoscope 3, to determine whether the specific instruments 9 in the image are arranged in any one of the reference configurations according to the image captured by the endoscope 3 and the configuration data sets 411 stored in the first database 41, and to drive the kinematic chain 22 to move the endoscope 3 to a specific position when it is determined that the specific instruments 9 are arranged in a matched one of the reference configurations. Specifically, when the endoscope 3 is at the specific position, the target point 422 of one of the target point sets 421 corresponding to the matched one of the reference configurations is at a central point of an image captured by the endoscope 3. The control unit 4 may be, for example, a computer or an electric circuit that can implement the functions described above. It should be noted that the control unit 4 is not limited to the above examples.

In this embodiment, one of the reference configurations is associated with an arrangement of the specific instruments 9 crossing each other, and the target point 422 corresponding thereto is close to a cross point of the specific instruments 9 (see FIG. 5). In some embodiments, the target point 422 may be located nearby the working end 91 of one of the specific instruments 9 (see FIG. 6.

In use, the endoscopic system is used to perform an endoscopic surgery (for example, a laparoscopic surgery) on a patient 7 by a user 8. The specific instruments 9 are surgical instruments which the user 8 is using for operating the endoscopic surgery.

During the endoscopic surgery, the control unit 4 controls the display device 5 to display a real-time image captured by the endoscope 3.

Referring to FIGS. 4 to 9, a method for controlling the endoscopic system during the endoscopic surgery is described in the following.

Figure 8:
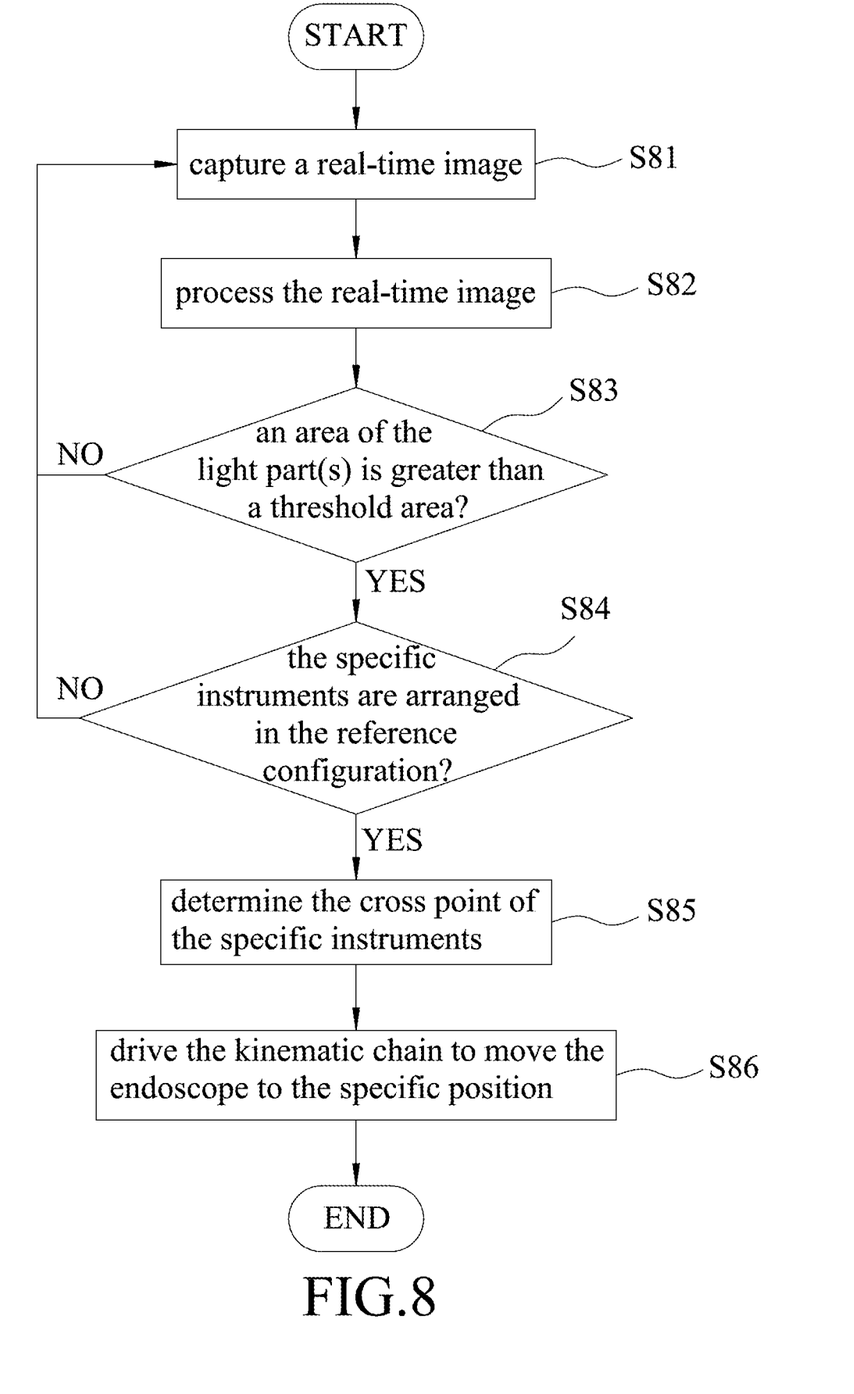
FIG. 8 is a flowchart of a method for controlling the endoscopic system according to one embodiment of this disclosure.
Figure 9:
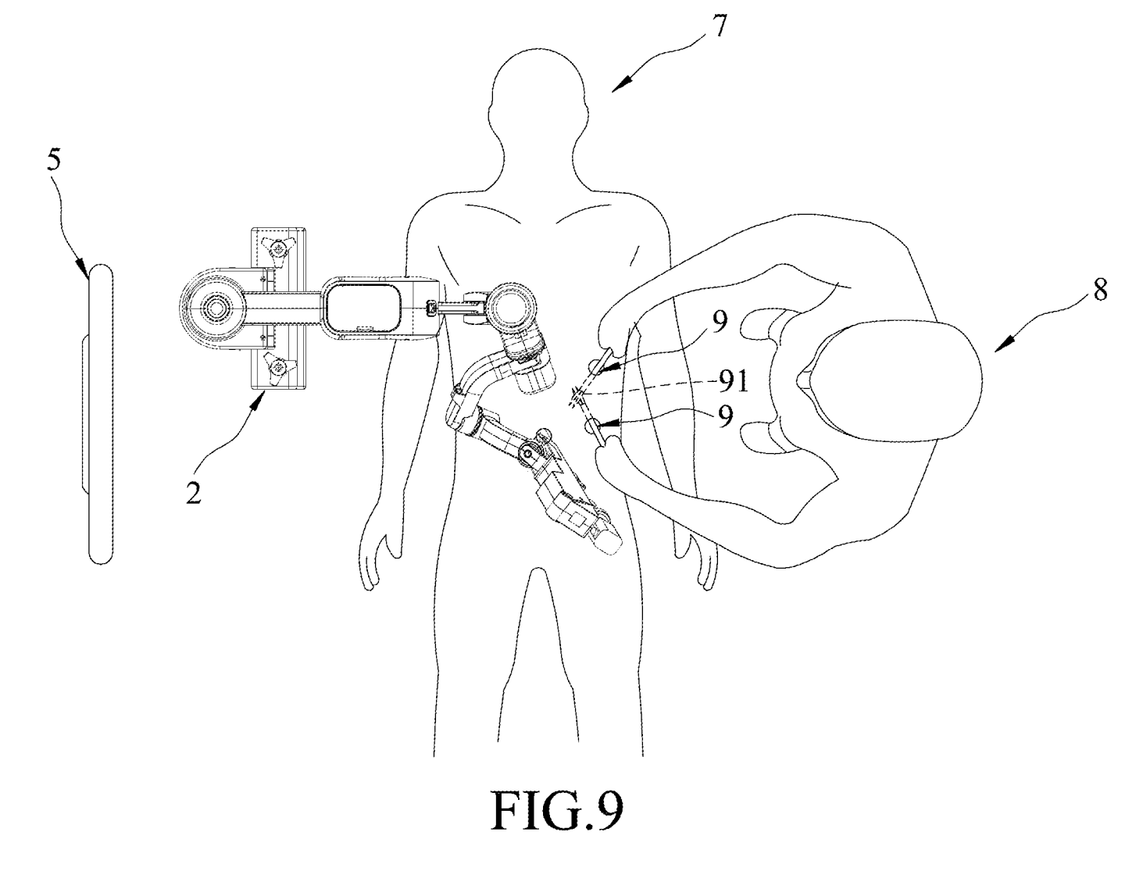
FIG. 9 is another top view of the endoscopic system.

In step S81, the endoscope 3 captures a real-time image of surgical environment of a human body during the endoscopic surgery.

In step S82, the control unit 4 receives the real-time image captured by the endoscope 3, and processes the real-time image by transforming to color space and by thresholding. As a result, the processed image may have at least a dark part (e.g., a black part) and a light part (e.g., a white part). In practice, a fixed constant (i.e., a threshold value) for implementing the thresholding is selected such that the specific instruments 9 in the real-time image captured by the endoscope 3 are transformed into the light part(s) in the processed image.

Then, in step S83, the control unit 4 determines whether an area of the light part(s) is greater than a threshold area. When the determination is negative, it means that there is no specific instruments 9 in the image, the control unit 4 does not drive the kinematic chain 22 to move the endoscope 3, and the flow goes back to step S81 for receiving another real-time image. When the determination is affirmative, it means that the specific instruments are present in the image (see FIGS. 4 to 6), the control unit 4 determines that positions of the light parts are positions of the specific instruments 9, and the flow goes to step S84.

In step S84, the control unit 4 further determines whether the specific instruments 9 are arranged in any one of the reference configurations (e.g., in a crossing configuration) according to shape(s) of the light part(s). When the determination is negative (see FIG. 4), the control unit 4 does not drive the kinematic chain 22 to move the endoscope 3, and the flow goes back to step S81 for receiving another real-time image. On the other hand, when the determination is affirmative (see FIG. 5 or 6), and the flow goes to step S85.

The following description of step S85 will be made assuming that said one of the reference configurations which the arrangement of the specific instruments 9 in the image matches is the crossing configuration. In step S85, the control unit 4 determines the cross point of the specific instruments 9 (see FIG. 5). For example, the control unit 4 analyzes the processed image to define a quadrilateral covering the light part, determines two diagonal lines of the quadrilateral that correspond to the specific instruments 9, respectively, and determines a cross point of the two diagonal lines as the cross point of the specific instruments 9. In some embodiments where the target point 422 is located at the working end 91 of one of the specific instruments 9 (see FIG. 6), the control unit 4 determines, in step S85, the working end 91 by determining at least an upper-left angle or an upper-right angle of the quadrilateral as the working end 91.

Figure 7:
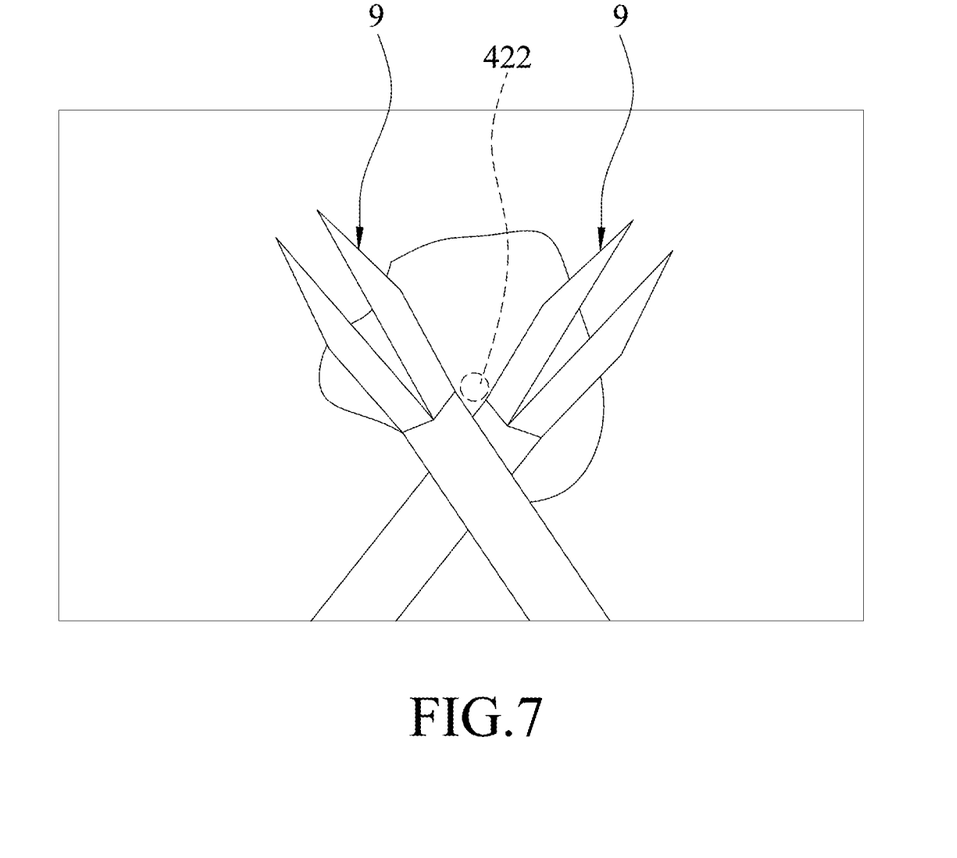

In step S86, the control unit 4 drives the kinematic chain 22 to move the endoscope 3 to the specific position where the real-time image captured by the endoscope 3 would be centered at the target point 422 (see FIG. 7). Accordingly, the user 8 can clearly observe an area near the target point 422 on the display device 5. In some embodiments, the target point set 421 corresponding to the matched one of the reference configurations may include a sequence of target points, and the control unit 4 drives, in step S86, the kinematic chain 22 to move the endoscope 3 sequentially to multiple positions respectively corresponding to the target points of the sequence. At each of the multiple positions, the image captured by the endoscope 3 would be centered at the respective one of the target points.

It should be noted that the endoscopic system can not only be used in a surgical operation but also be used in industrial environments.

In sum, when the user 8 uses the endoscopic system during an endoscopic surgery, the endoscope 3 can stay stationary to provide stable real-time images to the user 8 as long as the user 8 does not manipulate the specific instruments 9 to, for example, cross each other. When the user 8 intends to move the endoscope 3, the user 8 may, in this example, cross the specific instruments 9 (see FIG. 9) to activate automatic movement of the endoscope 3, under control of the control unit 4, to the specific position such that the central point of the image is nearby, in this example, the cross point of the specific instruments 9. Therefore, by using the endoscopic system according to this disclosure, disruption of the endoscopic surgery due to undesirable movement of the endoscope 3 is prevented.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An endoscopic system comprising:
a mechanical arm including a base, a kinematic chain connected to said base and movable with respect to said base, and a holding part connected to an end of said kinematic chain opposite to said base;
an endoscope held by said holding part and configured to capture an image; and
a control unit electrically connected to said kinematic chain and said endoscope, and configured to receive and process a first image captured by said endoscope, to determine whether the first image has at least two specific instruments that are arranged in a crossing configuration where the at least two specific instruments cross each other, and to, upon determining that the first image has at least two specific instruments that are arranged in the crossing configuration, drive said kinematic chain to move said endoscope to a specific position such that a central point of a second image captured by said endoscope having moved to the specific position is at a predetermined position relative to the crossing configuration,
wherein said control unit includes a first database storing a crossing configuration data set representative of the crossing configuration, and a second database storing a specific target point that includes a target point located at the predetermined position relative to the crossing configuration, and
wherein said control unit is further configured to
determine whether the at least two specific instruments in the first image are arranged in the crossing configuration according to the first image captured by said endoscope and the crossing configuration data set stored in said first database, and
upon determining that the at least two specific instruments in the first image are arranged in the crossing configuration, drive said kinematic chain to move said endoscope to the specific position where the target point is at the central point of the second image captured by said endoscope moved to the specific position.

2. The endoscopic system of claim 1, wherein said first database stores a plurality of configuration data sets representative of a plurality of reference configurations, respectively, and said second database stores a plurality of target point sets corresponding to the configuration data sets, respectively, wherein the reference configurations are related to different relative arrangements of the at least two specific instruments, the crossing configuration data set is one of the configuration data sets stored in said first database, the crossing configuration is one of the reference configurations, the specific target point set is one of the target point sets stored in said second database, and each of the target point sets includes a respective target point located at a respective position relative to one of the reference configurations that the corresponding one of the configuration data sets represents;
wherein said control unit is configured to
determine whether the at least two specific instruments in the first image are arranged in any one of the reference configurations according to the image captured by said endoscope and the configuration data sets stored in said first database, and
upon determining that the at least two specific instruments in the first image are arranged in one of the reference configurations, drive said kinematic chain to move said endoscope to a target position where the respective target point of one of the target point sets that corresponds to one of the configuration data sets representative of said one of the reference configurations is at a central point of another image captured by said endoscope moved to the target position.

3. The endoscopic system of claim 1, wherein the target point is nearby a cross point of the at least two specific instruments.

4. The endoscopic system of claim 1, wherein the target point is nearby a working end of one of the at least two specific instruments.

5. A method for controlling an endoscopic system, the endoscopic system including a mechanical arm, an endoscope held by the mechanical arm, and a control unit electrically connected to the mechanical arm and the endoscope, the method comprising steps of:
a) capturing, by the endoscope, a first image;
b) processing, by the control unit, the first image captured by the endoscope to determine whether the first image has at least two specific instruments that are arranged in a crossing configuration where the at least two specific instruments cross each other; and
c) when the determination made in step b) is affirmative, driving, by the control unit, the mechanical arm to move the endoscope to a specific position such that a central point of a second image captured by said endoscope having moved to the specific position is at a predetermined position relative to the crossing configuration,
wherein the control unit stores a crossing configuration data set representative of the crossing configuration, and a specific target point set corresponding to the crossing configuration data set and including a target point located at the predetermined position,
wherein step b) is to determine whether the at least two specific instruments in the first image are arranged in the crossing configuration according to the first image and the crossing configuration data set, and step c) is to drive the mechanical arm to move the endoscope to the specific position where the target point is at the central point of the second image captured by the endoscope moved to the specific position.

6. The method of claim 5, the control unit storing a plurality of configuration data sets representative of a plurality of reference configurations, respectively, and a plurality of target point sets corresponding to the configuration data sets, respectively, wherein the reference configurations are related to different relative arrangements of the at least two specific instruments, the crossing configuration data set is one of the configuration data sets, the crossing configuration is one of the reference configurations, the specific target point set is one of the target point sets, and each of the target point sets includes a respective target point located at a respective position relative to one of the reference configurations that the corresponding one of the configuration data sets represents;
wherein said method further comprises:
determining whether the at least two specific instruments in the first image are arranged in any one of the reference configurations according to the first image and the configuration data sets; and
upon determining that the at least two specific instruments in the first image are arranged in one of the reference configurations, driving the mechanical arm to move the endoscope to a target position where the respective target point of one of the target point sets that corresponds to one of the configuration data sets representative of said one of the reference configurations is at a central point of another image captured by the endoscope having moved to the target position.

7. The method of claim 5, wherein the target point is nearby a cross point of the at least two specific instruments.

8. The method of claim 5, wherein the target point is nearby a working end of one of the at least two specific instruments.

* * * * *